United States Patent
Dubuffet et al.

(10) Patent No.: US 7,157,484 B2
(45) Date of Patent: Jan. 2, 2007

(54) METHOD FOR SYNTHESISSING (2S, 3AS, 7AS)-PERHYDROINDOLE-2-CARBOXYLIC ACID AND THE ESTERS THEREOF AND THE USE THEREOF FOR PERINDOPRIL SYNTHESIS

(75) Inventors: Thierry Dubuffet, Autretot (FR); Pascal Langlois, Saint Jean de la Neuville (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 6 days.

(21) Appl. No.: 10/546,967

(22) PCT Filed: Feb. 27, 2004

(86) PCT No.: PCT/FR2004/000444

§ 371 (c)(1),
(2), (4) Date: Aug. 24, 2005

(87) PCT Pub. No.: WO2004/078707

PCT Pub. Date: Sep. 16, 2004

(65) Prior Publication Data

US 2006/0167273 A1    Jul. 27, 2006

(30) Foreign Application Priority Data

Feb. 28, 2003  (EP)  .................... 03290487

(51) Int. Cl.
A61K 31/403  (2006.01)
C07D 209/12  (2006.01)

(52) U.S. Cl. ...................... 514/412; 548/452

(58) Field of Classification Search ............... 514/412; 548/452

See application file for complete search history.

(56) References Cited

U.S. PATENT DOCUMENTS 4,933,361 A    6/1990  Holger et al.

2006/0149082 A1 *    7/2006  Dubuffet et al. ............ 548/492

FOREIGN PATENT DOCUMENTS

| EP | 0937714 A | 8/1999 |
|---|---|---|
| WO | WO 01/58868 | 8/2001 |
| WO | WO03/016336 | 2/2003 |

OTHER PUBLICATIONS

M Wincent, et al. "Stereoselective Synthesis of a New Perhydroindole Derivative of Chiral Iminodiacid, a Potent Inhibitor of Agiotensin Converting Enzyme", Tetrahedron, vol. 23, No. 16, p. 1677-1680, 1982.
International Search Report: PCT FR2004 000444, Aug. 9, 2004.
International Preliminary Examination Report: PCT 2004 000444, Aug. 31, 2004.
International Preliminary Report on Patentability: PCT/FR2004/000444—Sep. 29, 2005.

* cited by examiner

Primary Examiner—Golam M. M. Shameem
Assistant Examiner—Michael P. Barker
(74) Attorney, Agent, or Firm—Hueschen and Sage

(57) ABSTRACT

Process for the synthesis of compounds of formula (I):

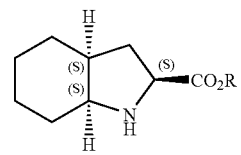

(I)

wherein R represents hydrogen or a protecting group.

Application in the synthesis of perindopril and pharmaceutically acceptable salts thereof.

6 Claims, No Drawings

METHOD FOR SYNTHESISSING (2S, 3AS, 7AS)-PERHYDROINDOLE-2-CARBOXYLIC ACID AND THE ESTERS THEREOF AND THE USE THEREOF FOR PERINDOPRIL SYNTHESIS

The present invention relates to a process for the synthesis of (2S, 3aS, 7aS)-perhydroindole-2-carboxylic acid and esters thereof, and to their application in the synthesis of perindopril and pharmaceutically acceptable salts thereof.

More specifically, the present invention relates to a new process for the synthesis of compounds of formula (I):

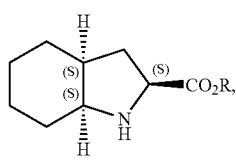
(I)

wherein R represents a hydrogen atom or a protecting group for the acid function, and addition salts thereof with a mineral or organic acid or base.

Among the protecting groups for the acid function there may be mentioned, without implying any limitation, benzyl and linear or branched ($C_1$–$C_6$)alkyl groups.

The compounds of formula (I) obtained in accordance with the process of the invention are useful in the synthesis of perindopril of formula (II):

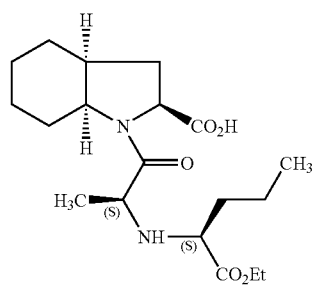
(II)

and in the synthesis of pharmaceutically acceptable salts thereof.

Perindopril and salts thereof have valuable pharmacological properties.

Their principal property is that of inhibiting angiotensin I converting enzyme (or kininase II), which prevents, on the one hand, conversion of the decapeptide angiotensin I to the octapeptide angiotensin II (a vasoconstrictor) and, on the other hand, degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in the European Patent specification EP 0 049 658.

In view of the pharmaceutical value of this compound, it has been important to obtain the intermediate of formula (I) by an effective synthesis process that allows the (S, S, S) diastereoisomer to be obtained selectively in a good yield and with excellent purity, starting from reasonably priced starting materials.

Some methods for the preparation of compounds of formula (I) are already known.

For example, the patent specification EP 0 037 231 uses indole-2-carboxylic acid as starting material, which is subjected to catalytic hydrogenation over rhodium to yield a mixture of the two cis endo isomers having the respective configurations (2S, 3aS, 7aS) and (2R, 3aR, 7aR). That mixture is then separated in especially laborious manner: synthesis of the N-benzoylated compound, fractional crystallisation of the salt of the diastereoisomer using (S)-α-phenyl-ethylamine, liberation of the two (S, S, S) and (R, R, R) N-benzoylated compounds and then removal of the benzoyl group, followed by passage over an ion-exchange column and recrystallisation.

For the same separation, the patent specification EP 0 115 345 uses several steps, requiring esterification of the carboxylic acid function by benzyl alcohol, conversion of the amino ester into a salt using N-benzyloxycarbonyl-(S)-phenylalanine, separation of the (S, S, S) isomer by fractional crystallisation, liberation of the aminated function, optionally followed by liberation of the carboxylic acid group.

The patent specifications EP 0 308 339 and EP 0 308 341 also use indole-2-carboxylic acid as starting material, which is first reduced to indoline-2-carboxylic acid to yield a mixture of 2R- and 2S-indoline-carboxylic acid, which are then separated by fractional crystallisation. The 2S isomer is then subjected to catalytic hydrogenation to yield the compound of formula (I).

The Applicant has now developed a new process for the synthesis of compounds of formula (I) starting from an especially reasonably priced starting material and allowing the (S, S, S) diastereoisomer to be obtained selectively in a good yield and with excellent purity.

More specifically, the present invention relates to a process for the synthesis of compounds of formula (I), characterised in that 1-(1-cyclohexen-1-yl)-pyrrolidine of formula (III):

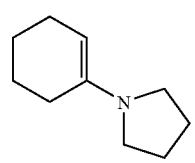
(III)

is reacted with the compound of formula (IV):

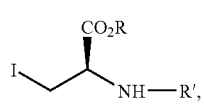
(IV)

wherein R is as defined for formula (I) and R' represents a protecting group for the amine function which is different from R, to yield the compound of formula (V):

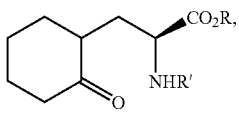

wherein R and R' are as defined hereinbefore, the amine function of which is deprotected before cyclisation is carried out, followed by dehydration, to yield the compound of formula (VI):

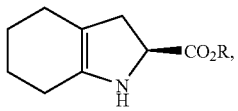

wherein R is as defined hereinbefore, which is subjected to catalytic hydrogenation, in the presence of a catalyst such as platinum, palladium, rhodium or nickel, under a pressure of from 1 to 30 bars, preferably from 1 to 10 bars, to yield, after optional deprotection or reprotection of the acid function, the compound of formula (I).

The compound of formula (I) thereby obtained has very good chemical and enantiomeric purity, making its use in the synthesis of perindopril of formula (II) especially advantageous.

By way of illustration, coupling of the compound of formula (I) obtained according to the process of the invention with the compound of formula (VII):

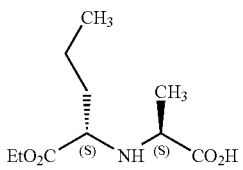

allows perindopril of formula (II) to be obtained with highly satisfactory purity and in a highly satisfactory yield.

The Examples hereinbelow illustrate the invention but do not limit it in any way.

EXAMPLE 1

(2S, 3aS, 7aS)-Perhydroindole-2-carboxylic acid

Step A: Benzyl (2S)-2-[(tert-butoxycarbonyl)-amino]-3-(2-oxocyclohexyl)-propanoate Introduce 200 g of 1-(1-cyclohexen-1-yl)-pyrrolidine, 535 g of benzyl (2S)-2-[(tert-butoxycarbon-3-iodopropanoate and 1.5 liters of acetonitrile into a reactor equipped with a reflux column.

Reflux for 1 hour and then return the mixture to ambient temperature. After evaporating off the solvent, add 2 liters of water and then acetic acid. Extract with ethyl acetate and evaporate to dryness. Benzyl (2S)-2-[(tert-butoxycarbonyl)-amino]-3-(2-oxocyclohexyl)-propanoate is obtained in that manner in a yield of 80%.

Step B: Benzyl (2S)-2-amino-3-(2-oxocyclohexyl)-propanoate

Introduce 200 g of the compound obtained in the previous Step, 1.5 liters of dichloromethane and 60 g of trifluoroacetic acid into a reactor. After stirring for 1 hour 30 minutes at ambient temperature, add 2 liters of saturated sodium hydrogen carbonate solution. Extract with dichloromethane and evaporate to dryness.

Benzyl (2S)-2-amino-3-(2-oxocyclohexyl)-propanoate is obtained in that manner in a yield of 90%.

Step C: Benzyl (2S)-2,3,4,5,6,7-hexahydro-1H-indole-2-carboxylate

In a reactor, reflux 200 g of the compound obtained in the previous Step, 13.8 g of p-toluenesulphonic acid and 1 liter of toluene, the water formed being removed by azeotropic distillation. When no more water is separated off, evaporate off the toluene.

Benzyl (2S)-2,3,4,5,6,7-hexahydro-1H-indole-2-carboxylate is obtained in that manner in a crude yield of 97%.

Step D: (2S, 3aS, 7aS)-Perhydroindole-2-carboxylic acid

Introduce 200 g of the compound obtained in the previous Step, dissolved in acetic acid, and then 5 g of Pt/C 10% into a hydrogenator. Hydrogenate under a pressure of 5 bars at ambient temperature until the theoretical amount of hydrogen has been absorbed. Remove the catalyst by filtration and then cool to a temperature of from 0 to 5° C. and collect the resulting solid by filtration. Wash the filter cake and dry it to constant weight. (2S, 3aS, 7aS)-Perhydroindole-2-carboxylic acid is obtained in that manner in a yield of 87% and with an enantiomeric purity of 99%.

EXAMPLE 2

Benzyl (2S, 3aS, 7aS)-perhydroindole-2-carboxylate para-toluene-sulphonate

In a reactor, reflux 200 g of the compound of Example 1, 800 g of para-toluenesulphonic acid, 227 g of benzyl alcohol and 700 ml of toluene, the water formed being continuously removed with the aid of a separator. When no more water is separated off, cool, filter off the resulting precipitate under suction and dry.

Benzyl (2S, 3aS, 7aS)-perhydroindole-2-carboxylate para-toluenesulphonate is obtained in that manner in a yield of 91% and an enantiomeric purity of 99%.

The invention claimed is:

1. A process for the synthesis of compounds of formula (I):

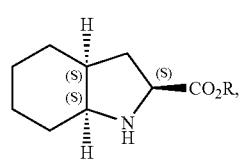

wherein R represents hydrogen or a protecting group, wherein 1-(1-cyclohexen-1-yl)-pyrrolidine of formula (III):

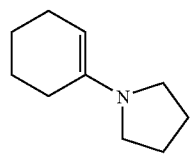

(III)

is reacted with a compound of formula (IV):

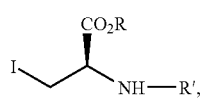

(IV)

wherein R is as defined for formula (I) and R' represents a protecting group which is different from R, to yield a compound of formula (V):

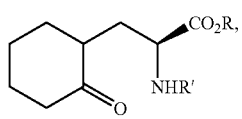

(V)

the amine function of the compound of formula (V) is deprotected and the deprotected intermediate thus obtained is subjected to dehydration, to yield a compound of formula (VI):

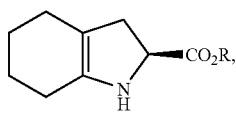

(VI)

which is subjected to catalytic hydrogenation, in the presence of a catalyst, under a pressure of from 1 to 30 bars, to yield, after optional deprotection or reprotection of the acid function, the compound of formula (I).

2. The process of claim 1, wherein the hydrogen pressure during the hydrogenation reaction is from 1 to 10 bars.

3. The process of claim 1, wherein the catalyst is selected from palladium, platinum, rhodium and nickel.

4. The process of claim 1, wherein R represents hydrogen.

5. The process of claim 1, wherein R represents benzyl.

6. A process for the synthesis of perindopril or a pharmaceutically acceptable salt thereof, wherein the compound of formula (III) is converted into the intermediate compound of formula (I) according to the process of claim 1, and the intermediate compound of formula (I) is converted into perindopril or a pharmaceutically acceptable salt thereof.

* * * * *